United States Patent
Wyman et al.

(10) Patent No.: US 9,308,165 B2
(45) Date of Patent: Apr. 12, 2016

(54) COMPOSITION FOR TREATING OCULAR EFFECTS OF DIABETES

(71) Applicant: THERAPEUTIC VISION, INC., Omaha, NE (US)

(72) Inventors: Milton Wyman, Powell, OH (US); Vincent Bellavia, Waterdown (CA)

(73) Assignee: THERAPEUTIC VISION, INC., Omaha, NE (US)

( * ) Notice: Subject to any disclaimer, the term of this patent is extended or adjusted under 35 U.S.C. 154(b) by 0 days.

(21) Appl. No.: 13/974,027

(22) Filed: Aug. 22, 2013

(65) Prior Publication Data
US 2015/0057323 A1 Feb. 26, 2015

(51) Int. Cl.
A61K 9/06 (2006.01)
A61K 31/4188 (2006.01)
A61K 9/00 (2006.01)
A61K 47/32 (2006.01)

(52) U.S. Cl.
CPC .............. *A61K 9/06* (2013.01); *A61K 9/0048* (2013.01); *A61K 31/4188* (2013.01); *A61K 47/32* (2013.01)

(58) Field of Classification Search
None
See application file for complete search history.

(56) References Cited

U.S. PATENT DOCUMENTS

| | | | |
|---|---|---|---|
| 8,158,667 B2 | 4/2012 | Kador et al. | |
| 2001/0036966 A1* | 11/2001 | Yasueda et al. | 514/781 |
| 2003/0050301 A1 | 3/2003 | Mylari | |
| 2003/0186994 A1 | 10/2003 | Mylari | |
| 2004/0071778 A1* | 4/2004 | Bellmann et al. | 424/488 |
| 2006/0292099 A1* | 12/2006 | Milburn et al. | 424/70.1 |
| 2009/0082415 A1 | 3/2009 | Kador et al. | |
| 2012/0094962 A1* | 4/2012 | Skulachev | 514/125 |

FOREIGN PATENT DOCUMENTS

IT 1247560 B 12/1994

OTHER PUBLICATIONS

Walsh et al. (JAMA 2002;287(14):1840-1847).*
Torok et al., (J Drugs Dermatol. 2011;10(6):647-652).*

Peter F. Kador et al., "Topical Kinostat™ Ameliorates the Clinical Development and Progression of Cataracts in Dogs with Diabetes Mellitus", *Vet Ophthalmol.* Nov. 2010; 13(6): 363-368.
"Carbomer 980 0.2% Liquid Eye Gel", Patient Information Leaflet, Dec. 2012, 2 pages.
"Pharmaceutical Polymers for Liquid and Semisolid Dosage Forms", Lubrizol Advanced Materials, Inc., 2011, 12 pages.

* cited by examiner

*Primary Examiner* — Patricia Duffy
*Assistant Examiner* — Garen Gotfredson
(74) *Attorney, Agent, or Firm* — Richard C. Litman

(57) ABSTRACT

The composition for treating ocular effects of diabetes is a composition that contains an aldose reductase inhibitor in an ophthalmic gel for topical application to the eye. The composition includes a carrier having, by weight, about 0.4% carbomer, 4.0% sorbitol, 0.01% centrimide, 0.01% ethylenediaminetetraacetic acid (EDTA) and effective amounts of sodium chloride and sodium hydroxide for adjusting the pH of the topical carrier to about 7 and to achieve a desired viscosity, with the balance being water. The aldose reductase inhibitor (ARI) is mixed with the topical carrier at about 0.1%-6% by weight of the composition to form an ophthalmic gel. Preferably, the ARI is 2R,4S-6-fluoro-2-methyl-spiro [chroman-4,4'-imidazolidine]-2',5'-dione, referred to as 2-methyl sorbinil, having the structure:

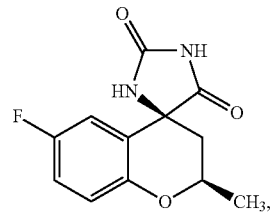

or a pharmaceutically acceptable salt thereof. In use, the ophthalmic gel is preferably applied as an eye drop at a dosage of one drop per eye administered two to three times daily.

18 Claims, No Drawings

COMPOSITION FOR TREATING OCULAR EFFECTS OF DIABETES

STATEMENT REGARDING FEDERALLY SPONSORED RESEARCH OR DEVELOPMENT

This invention was made with government support under NIH SBIR Phase 2 grant number R44 EY018013-02A1, awarded by the National Institutes of Health. The government has certain rights in this invention.

BACKGROUND OF THE INVENTION

1. Field of the Invention

The present invention relates to the treatment of complications of diabetes, and particularly to a composition for treating ocular effects of diabetes.

2. Description of the Related Art

In the United States, companion pets number over 62 million dogs and 71 million cats. According to the American Veterinary Medical Association (AVMA), these dogs and cats are living longer due to better nutrition and preventive veterinary care. With over 40% of this population being at least seven years old, more pets are being diagnosed with diabetes mellitus (DM). Although DM occurs at any age, it most frequently is diagnosed in dogs and cats between the ages seven and nine. In 1996, the prevalence of DM in dogs and cats was reported to range between 0.2-1%, i.e., approximately 1 in every 200 dogs and cats was diabetic. A number of complications result from diabetes mellitus, including the formation of cataracts; diabetic retinopathy; corneal lesions, erosion, wound healing complications, epithelial barrier changes, and other corneal pathology; changes in the iris (delay in dilation, fibrous tissue formation, altered vessel permeability, etc.); morphological changes in the ciliary bodies; and other diabetic changes.

Investigations have shown that many of the complications of diabetes result, at least in part, from abnormalities in glucose metabolism through the polyol pathway. Normally the bulk of intracellular glucose is metabolized to provide energy by phosphorylation of glucose, which is catalyzed by hexokinase to form glucose-6-phosphate, which is further metabolized to useful energy by entry into the Krebs cycle. In the diabetic patient, however, insufficient hexokinase is available to metabolize all of the intracellular glucose.

In many tissues of the body, including lens tissue in the eye, an alternative path is available to metabolize glucose. The enzyme aldose reductase (AR) catalyzes the reduction of glucose to sorbitol with hydrogen supplied by NADPH. Sorbitol is then oxidized to fructose by sorbitol dehydrogenase, the hydrogen being accepted by NAD+. However, in the hyperglycemic patient, although sufficient aldose reductase is available to reduce glucose to sorbitol, there is not sufficient sorbitol dehydrogenase to oxidize the sorbitol to fructose.

This leads to an accumulation of sorbitol in the tissues. Sorbitol does not readily diffuse through the tissues and cellular membranes due to its polarity. It is hypothesized that the accumulation of sorbitol produces a hyperosmotic condition, with resulting fluid accumulation in the cells, altering membrane permeability with the development of the pathological conditions noted above. Consequently, considerable attention has focused on the development of aldose reductase inhibitors (ARIs).

With diabetic dogs being prone to develop bilateral cataracts, research into the development thereof has shown that this is related to AR levels in the lens. Research studies have also shown that the oral administration of aldose reductase inhibitors to dogs have been effective in the prevention of cataracts resulting from diabetes, as well as in the treatment of diabetic retinopathy, corneal lesions, and other complications of diabetes mellitus.

Nevertheless, the oral administration of aldose reductase inhibitors has several shortcomings. The dosage of ARIs administered orally is rather high (about four times per day), and must be maintained over a long period of time. Oral administration requires processing by the liver, and may compromise the dog's liver function. Moreover, no studies have yet shown reversal of the formation of cataracts in dogs from the oral administration of aldose reductase inhibitors.

It would be desirable to provide a topical formulation for administering an ARI directly into the dog's eyes. Conventional topical formulations for ARIs are not effective for use on dogs, since such formulations are generally aqueous solutions, and tear flow in dogs is generally greater than in humans, so that it is not possible to maintain therapeutic levels of an ARI, since such formulations are washed out by tear formation. A topical formulation for the administration of an ARI directly into a dog's eyes would be desirable for reduction of dosage and frequency of administration, quicker absorption into the system, and avoiding liver metabolism of the ART.

U.S. Pat. No. 8,158,667, issued Apr. 17, 2012 to Kador et al., describes a topical composition for the treatment of optical complications of diabetes in dogs that comprises a carrier having a specific composition and an aldose reductase inhibitor mixed with the carrier to form an ophthalmic gel. (One of the present inventors, Dr. Milton Wyman, was also a co-inventor in the '667 patent, which is hereby incorporated by reference in its entirety.) A preferred ARI named in the '667 patent is methyl sorbinil, and more particularly preferred, the isomer 2-methyl sorbinil. While the composition of the '667 patent is effective in the treatment of optical complications of diabetes in dogs to the extent described therein, it has been found that the specific carrier described in the '667 patent does not deliver a sufficiently therapeutic amount of the ARI to the dog's eye to exert a preventive, inhibitory, or prophylactic effect to the extent desired. Improvement in the carrier or vehicle of the '667 is therefore desirable.

Thus, a composition for treating ocular effects of diabetes solving the aforementioned problems is desired.

SUMMARY OF THE INVENTION

The composition for treating ocular effects of diabetes is a composition that contains an aldose reductase inhibitor in an ophthalmic gel for topical application to the eye. The composition includes a carrier having, by weight, about 0.4% carbomer, 4.0% sorbitol, 0.01% centrimide, 0.01% ethylenediaminetetraacetic acid (EDTA) and effective amounts of sodium chloride and sodium hydroxide for adjusting the pH of the topical carrier is about 7 and to achieve a desired viscosity, with the balance being water. The aldose reductase inhibitor (ARI) is mixed with the topical carrier at about 1%-6% by weight of the composition to form an ophthalmic gel. Preferably, the ARI is 2R,4S-6-fluoro-2-methyl-spiro[chroman-4,4'-imidazolidine]-2',5'-dione, referred to as 2-methyl sorbinil, having the structure:

or a pharmaceutically acceptable salt thereof. In use, the ophthalmic gel is preferably applied as an eye drop at a dosage of one drop per eye administered two to three times daily.

It should be understood that the present composition may be used for treatment of ocular diabetic complications, including keratopathy, cataracts and retinopathy, both in animals and in human beings. For dogs, the aldose reductase inhibitor (ARI) is mixed with the topical carrier at about 3%-6% by weight of the composition to form the ophthalmic gel. Although the present composition was originally designed as a viscous formulation to overcome the problem of excessive tear flow in dogs, aldose reductase levels in dogs and humans are similar, and human children also experience excessive tear flow similar to tear flow in dogs. The viscous nature of the formulation, however, increases the corneal retention time to the extent that a lower concentration of the ARI is required for humans, preferably about 0.1-3% by weight.

These and other features of the present invention will become readily apparent upon further review of the following specification and drawings.

DETAILED DESCRIPTION OF THE PREFERRED EMBODIMENTS

The composition for treating ocular effects of diabetes is a composition that contains an aldose reductase inhibitor in an ophthalmic gel for topical application to the eye. The composition includes a carrier having, by weight, about 0.4% carbomer, 4.0% sorbitol, 0.01% centrimide, 0.01% ethylenediaminetetraacetic acid (EDTA) and effective amounts of sodium chloride and sodium hydroxide for adjusting the pH of the topical carrier to about 7 and to achieve a desired viscosity, with the balance being water. The aldose reductase inhibitor (ARI) is mixed with the topical carrier at about 1%-6% by weight of the composition to form an ophthalmic gel. Preferably, the ARI is 2R,4S-6-fluoro-2-methyl-spiro [chroman-4,4'-imidazolidine]-2',5'-dione, referred to as 2-methyl sorbinil, having the structure:

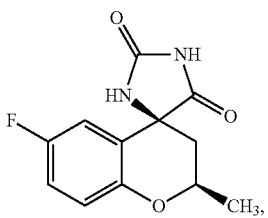 [SMILES: C[C@@H]1C[C@]2(NC(=O)NC2=O)c2cc(F)ccc2O1]

or a pharmaceutically acceptable salt thereof. In use, the ophthalmic gel is preferably applied as an eye drop at a dosage of one drop per eye administered two to three times daily.

Diabetes mellitus (DM) is a group of metabolic disorders that are characterized by hyperglycemia. Central to the treatment of DM is the tight control of hyperglycemia to reduce the onset and development of long-term complications. These generally develop in tissues with insulin-independent glucose uptake, where glucose is rapidly phosphorylated by hexokinase and undergoes glycolysis. With hyperglycemia, excess glucose in these tissues enters the two step sorbitol pathway (polyol pathway) where it is converted to fructose. In the first step, glucose is reduced by the enzyme aldose reductase (AR) and its cofactor NADPH to the sugar alcohol sorbitol. In the second step, sorbitol is oxidized to fructose by sorbitol dehydrogenase (SDH) and its cofactor, $NAD^+$. Glucose is reduced to sorbitol faster than sorbitol is oxidized to fructose under hyperglycemic conditions. The net effect is the intracellular accumulation of excess sorbitol.

Both increased AR activity and the excess intracellular sorbitol formation have been directly linked to the onset and progression of diabetic complications. A similar biochemical mechanism occurs with galactosemia where AR rapidly reduces galactose to galactitol; however, galactitol it is not further metabolized by sorbitol dehydrogenase. As a result, galactitol is more rapidly formed and reaches higher intracellular tissue levels than sorbitol. In the eye, excess AR activity and the accumulation of either sorbitol or galactitol have been linked to a number of ocular complications.

The anterior surface of the eye is covered by the corneal epithelium and conjunctiva, with the limbus in-between. The clinical effects of uncontrolled diabetes mellitus on these tissues include decreased corneal sensitivity, increased corneal thickening, persistent stromal edema, and decreased tolerance to stress associated with photocoagulation, vitrectomy surgery, or even the wearing of contact lenses. Tear secretion is also significantly reduced in diabetics. The conjunctiva shows increased squamous metaplasia and lower goblet cell densities, along with the presence of neuropathy in the corneal nerves.

The diabetic cornea shows morphological changes in both corneal epithelial and endothelial cells, which include alterations in their size, shape, and number. There are also variations in the number of epithelial cells layers, areas of layer thinning, and decreased barrier function, AR is present in both of these cells. Studies in diabetic and galactose-fed rats and dogs, as well as clinically in diabetic humans, demonstrate that aldose reductase inhibitors are affective in ameliorating changes in both corneal epithelium and endothelium structure and function, and neuropathy in the corneal nerve fibers. This results in improving wound healing, reducing the hazy, edematous appearance of the healed corneas, reducing epithelial permeability, and restoring nerve sensitivity in the corneal epithelium. ARIs also reduce corneal thickening and persistent stromal edema suggestive of abnormal endothelial cell function, and also maintain the morphology of the endothelial cells. Clinically, ARIs have also been reported to also promote corneal healing in patients with corneal epithelial disorders unresponsive to conventional treatment.

Diabetes is associated with physical, refractive and cataractous changes of the lens. Sugar cataract formation is dependent on lens aldose reductase activity, which catalyzes the formation of sorbitol and galactitol from glucose and galactitol, respectively, Sugar cataract formation is initiated by the intracellular accumulation of sorbitol or galactitol in the lens, which leads to lens swelling, membrane permeation, vacuole and cleft formation, disturbance to the intracellular environment, protein aggregation/modification, and light scatter. Support for the "Osmotic Hypothesis" of sugar cataract development comes from lens culture and animal studies, as well as prevention studies in diabetic and galactosemic animals administered ARIs.

Bilateral cataracts develop in both diabetic and galactosemic dogs. These cataracts are the hallmark of DM in dogs, with the majority of dogs showing lens changes within 5-6 months after the diagnosis of DM. Cataracts not only result in vision loss and blindness, but require surgery because untreated canine cataracts can initiate lens-induced uveitis that results in intractable uveitis and painful glaucoma. While the success rate for cataract surgery in dogs ranges between 90-95%, the major drawback of canine cataract surgery is financial, since no insurance coverage is generally available. Post-surgical diabetic dogs also develop dry eye that is linked to corneal neuropathy.

Because AR levels in the lens decrease with age, sugar cataract development is faster and is more severe in children and young animals. Bilateral cataracts rapidly develop in galactosemic infants and children, and in adolescents with DM who are in poor glycemic control. In children, these cataracts are often referred to as "true" diabetic cataracts because they rapidly evolve over a period of days and generally appear simultaneously in both eyes. Similar bilateral sugar cataracts rapidly form after birth when a lactose diet is fed to galactosemic infants where an enzyme in the metabolism of galactose is deficient. When caught in their early stage, these cataracts can generally be reversed by removal of galactose from the diet.

While classic galactosemia is rare (an incidence of about 1 per 60,000 births), diabetes is one of the most common chronic diseases in pediatrics. Type 1 DM is most prevalent in young Caucasians, especially those of northern European ancestry, but a steady increase in the incidence of this disease has been reported in many parts of the world. There are two types of type 1 DM—an early onset type appearing at an average age of 2.6 years, and a later onset type at 9.9 years. New cases of type 1 diabetes are predicted to double in European children younger than 5 years, and the prevalence of such cases will likely increase by 70% in those younger than 15 years of age. Similar trends are suggested in the United States for non-Hispanic white youth.

In addition to type 1 DM, the prevalence of type 2 diabetes mellitus is increasing worldwide in children and adolescents. Linked with obesity, this is particularly prevalent in the U.S. among African American, American Indian, Hispanic and Asian/Pacific Islander youth. Also contributing to diabetes in children are genetic defects associated with MODY (maturity onset diabetes of the young). This monogenic and autosomal dominant form of DM generally occurs before the age of 25, but has been documented in children as young as 8 months of age.

Hyperglycemia is difficult to control in diabetic children, especially infants, where tiny doses of administered insulin can result in extremely variable blood sugar control with unpredictable fluctuations. Hyperglycemia is also difficult to control in type 2 or MODY children, since drugs used in adults are generally not successful in these children. It has been directed that children under the age of 13 should not be placed on a program of tight glycemic control because glucose is vital to brain development. Therefore, cataracts, as well as diabetic retinopathy, are anticipated to develop in these children. Even in older, poorly controlled children, the incidence of cataracts has been reported to be 20%.

Cataract development in children under the age of 5 is especially serious because cataracts can result in permanent vision loss due to irreversible or untreated amblyopia. Cataract surgery in young children can be problematic because their eyes may undergo significant ocular growth after surgery. Generally, in these young children the entire lens is removed, and contact lenses are used to restore aphakic vision because phacoemulsification and use of intraocular lenses (IDLs) are associated with correction problems in the growing eye, and because of a high rate of secondary cataracts due to posterior capsule opacification (PCO), which requires surgical membranectomy re-operations. When IOLs are used in children under the age of 5 years, it has been suggested that both an elective primary capsulotomy and elective anterior vitrectomy be mandatory so that a clear visual axis is maintained.

The development of diabetic retinopathy, which is characterized by vascular changes of the retinal capillary bed, is directly linked to the severity of hyperglycemia. The development of retinal capillary changes (microangiopathies) includes the appearance of the following histopathological and clinical lesions: selective pericyte loss, capillary basement membrane thickening, dilations/endothelial hypertrophy, permeability/hard exudates, capillary nonperfusion and occlusion/acellularity, microaneurysms/intraretinal hemorrhages, intraretinal microvascular abnormalities, ORMA shunts/dilated meshwork, cotton wool spots/ischemia, vessel-glial proliferation, extra retinal hemorrhages, glial-vitreal contraction, and macular edema. While many of these lesions are present in a number of ocular diseases, all of above-described lesions are only present together in DM.

The hallmark of diabetic retinopathy is the selective death of retinal capillary pericytes (mural cells or intramural pericytes) that contain AR and accumulate sugar alcohols. Exposure of pericytes to excess glucose or galactose results in apoptosis that is prevented by inhibition of AR with ARIs. Prevention studies in rats and dogs confirm that inhibition of AR prevents pericyte destruction, capillary basement membrane thickening, and the formation of acellular capillaries and subsequent areas of nonperfusion. Definitive evidence for the role of AR in initiating the early stages of DR comes from transgenic mice in which AR is either over-expressed or knocked out.

The development and progression of diabetic retinopathy in both human patients and in dogs requires years to develop. The progression of diabetic retinopathy is linked to the presence of AR alleles that are association with increased AR activity. This development is accelerated in galactosemic animals. For example, while retinopathy in diabetic dogs rarely progresses past the mild to moderate non-proliferative stage, retinal changes in galactose-fed dogs progress to the proliferative stage in essentially the same time period. Moreover, these retinal changes are prevented by administration of ARIs. Studies in dogs and rats suggest that the prevention of cataracts by adequate administration of ARIs may serve as a surrogate marker for the preservation of retinal pericytes.

Since the development and progression of diabetic retinopathy is directly linked to hyperglycemic control, the development of DR is anticipated to dramatically increase with the directive that children under the age of 13 should not be placed on a program of tight glycemic control. In addition, it is known that both the prepubertal and postpubertal years with diabetes contribute to the overall probability of DR development. In contrast to diabetics, retinal lesions in galactosemic children or adults are rare. This is because the rapid appearance of cataracts in infancy results in a life-long dietary restriction of galactose. Nevertheless, retinal changes have been documented (including vitreous hemorrhage likely associated with retinal hemorrhage) in five neonates with severe galactosemia, as well as bilateral intraretinal macular deposits in a patient with galactokinase deficiency and extremely high dietary intake of milk and its products.

Aldose reductase inhibitor (ARI) treatment requires adequate bioavailable levels of the drug in ocular target tissues. To achieve these intraocular levels by topical administration requires adequate retention of the ARI on the ocular surface so that absorption through the cornea and conjunctiva can be achieved. The cornea and conjunctiva, however, are protected by tears and the eyelid, whose function is to provide nutrition and oxygen to the corneal surface, to lubricate and remove foreign matter (including ophthalmic solutions or suspensions) from the corneal and conjunctival surfaces. Achieving adequate topical administration is especially difficult in dogs where tear flow is significantly higher than in humans.

While the composition described in U.S. Pat. No. 8,158,667, issued Apr. 17, 2012 to Kador et al., is effective in the treatment of optical complications of diabetes in dogs to the extent described therein, it has been found that the specific carrier described in the '667 patent does not deliver a sufficiently therapeutic amount of the ARI to the dog's eye to exert a preventive, inhibitory, or prophylactic effect to the extent desired. It will be understood that the terms "prevent", "prevention", and "preventive" do not mean that the present composition is 100% effective to the extent that cataracts or other ocular complications never appear after administration of the present composition. Rather, the terms "prevent", "prevention", and "preventive" mean that laboratory experiments and statistical studies have shown that populations of animals, and particularly dogs, who have exhibited risk factors (diagnosis of diabetes mellitus or galactosemia with or without pre-diabetic lesions or other signs in the tissues and lenses of the eyes, etc.) that would ordinarily be expected to develop severe ocular complications characteristic of the diabetic (or galactosemic) animal experience a statistically significant lower incidence of such severe complications after administration of the present composition to the extent that those of ordinary skill in the art may reasonably conclude that the composition exerts an inhibitory or prophylactic effect, or in common parlance, has some effect in preventing the complications in a statistically significant portion of the population being studied.

The present inventors have found that a therapeutic amount of the ART can be delivered to the dog's eye to exert a greater preventive, inhibitory, or prophylactic effect by a modification to the carrier. The present topical vehicle is composed of an aqueous solution containing by weight about 0.4% carbomer, 4.0% sorbitol, 0.01% centrimide, 0.01% ethylenediaminetetraacetic acid (EDTA) and effective amounts of sodium chloride and sodium hydroxide for adjusting the pH of the topical carrier to about 7 and to achieve a desired viscosity, with the balance being water. A representative example of the carrier contains, by weight, about 0.4% Carbopol 980, 3.78% sorbitol, 0.01% Cetrimide (cetrimonium bromide), 0.01% EDTA, and effective amounts of sodium chloride and sodium hydroxide to both adjust the viscosity and bring the pH of the mixture to 7.2. The vehicle has a viscosity of about 1,928 cps that is reduced to about 1,300 cps after the addition of the ARI, which may be any ARI, but is preferably about 5 wt % 2R,4-6-fluoro-2-methyl-spiro[chroman-4,4'-imidazolidine]-2',5'-dione (2'MS, or 2-methyl sorbinil)) with a standardized particle size of less than 10 microns.

Carbopol® 980 (carbopol is a registered trademark of Lubrizol Advanced Materials, Inc. of Cleveland, Ohio) is a crosslinked polyacrylate polymer that is a water-swellable polymer used as a thickening agent suitable for clear gels. Carbopol 980 has been used as the active ingredient in many formulations for the treatment of dry eyes, often in conjunction with sorbitol, cetrimide, EDTA, and sodium chloride, with dilute sodium hydroxide being used to adjust pH. However, the concentration of Carbopol 980 used in the present carrier is about twice the concentration used in such dry eye formulations in order to retain the ARI in the gel for a sufficient period of time to maintain therapeutic levels of the ARI in the dog's eyes.

It is noted that the purpose of the present composition is to prevent the accumulation of sorbitol in the dog's eyes, and yet the carrier contains sorbitol. However, the sorbitol in the carrier is not absorbed by the tissues of the eye, and therefore does not exacerbate the accumulation of sorbitol that results in ocular complications of diabetes. The sorbitol in the carrier is a hydroxyl group donor that hydrogen bonds to the carbomer, thereby increasing thickening and viscosity. It is also thought that the sorbitol prevents excessive crosslinking and web formation of the carbomer in the container, but is quickly dispersed and washed away by the film of tears in the dog's eyes upon application. EDTA and cetrimide are preservatives, while sodium chloride is used to adjust viscosity. Carbopol 980 reaches maximum viscosity at a pH of about 6-7, so that dilute sodium hydroxide (about 0.5N) is added dropwise to adjust pH. In use, the ophthalmic gel is applied to ocular target tissues in a dosage of between approximately two and approximately four drops daily.

In order to test the efficacy of the composition, a randomized, prospective, double-masked placebo control clinical study was conducted in 40 dogs, each being newly diagnosed with diabetes mellitus. The study population included twenty spayed female dogs and twenty neutered male dogs, ranging in ages between four and fourteen years, with a mean age of nine years, with the study population being gathered over a period of eighteen months. Twenty-eight dogs received the composition described above in both eyes, three times per day, and the remaining twelve dogs received a placebo. The placebo consisted of an identical topical carrier vehicle, emulsified with a non-nutritive starch so that the composition and the placebo could not be visually differentiated. The contents of coded vials were administered by the dog owners, after receiving training on topical administration of such agents, and compliance was monitored by having the owners maintain an administration log sheet.

Clinical ophthalmic examinations were conducted at the onset of the study, and also at one, two, three, six and twelve months after the onset of the study. The clinical examination included slit lamp and fundus examinations of the dilated eye, as well as the measurement of intraocular pressure and tear flow with the Schirmer tear test. Lens changes were graded on a scale of 0-3 as follows: "0" corresponds to an unchanged condition or no cataract formation; "1" corresponds to vacuoles mild progression or punctate anterior cortical cataracts;

"2" corresponds to cortical vacuoles or cortical opacities; and "3" corresponds to an advanced cataract.

At the start of the study, there was no significant difference in the presence of lens opacities (cataract score, mean±standard error of the mean (SEM)) between the placebo (0.73±0.06) and the composition (0.83±0.08) treated groups (p=0.297). All owners were instructed on the importance of achieving good glycemic control in their dogs and HbAlC values obtained after twelve months of treatment were not significantly different (p=0.369) between the placebo (6.7±0.95) and composition (7.7±1.8) groups.

After twelve months of treatment, lens changes were observed in 20 of 24 eyes receiving the placebo. Seven dogs (i.e., 14 eyes) developed advanced cataracts (scale 3), two dogs (i.e., 4 eyes) developed cortical opacities (scale 2), and one dog (i.e., 2 eyes) developed equatorial vacuoles/mild punctate cortical opacities (scale 1) with bilateral changes. Cataract formation was absent in two of twelve dogs (i.e., 16.7% of the placebo group). The population variance of the placebo group was not significantly different (p<0.13).

In contrast, in the dogs receiving the present composition, after twelve months of treatment, anterior equatorial vacuoles were present in 14 eyes, cortical opacities were present in 4 eyes, and advanced cataracts were present in 8 eyes, with all lens changes being bilateral. In the dogs with advanced cataracts, these developed within six months in three dogs, and by twelve months in one dog. After twelve months of treatment, the mean cataract severity score of the placebo group significantly increased from 0.73±0.06 to 2.17±0.34 (mean±SEM, p<0.0002), while the mean cataract severity score of the topical composition group showed no significant increases, going only from 0.83±0.08 to 0.88±0.14 after twelve months of treatment, which was significantly less (p=0.0016) than the mean cataract score of the twelve month placebo treated group (2.17±0.34).

It should be understood that the present composition may be used for treatment of ocular diabetic complications, including keratopathy, cataracts and retinopathy, both in animals and in human beings. For dogs, the aldose reductase inhibitor (ARI) is mixed with the topical carrier at about 3%-6% by weight of the composition to form the ophthalmic gel. Although the present composition was originally designed as a viscous formulation to overcome the problem of excessive tear flow in dogs, aldose reductase levels in dogs and humans are similar, and human children also experience excessive tear flow similar to tear flow in dogs. The viscous nature of the formulation, however, increases the corneal retention time to the extent that a lower concentration of the ARI is required for humans, preferably about 0.1-3% by weight.

It is to be understood that the present invention is not limited to the embodiments described above, but encompasses any and all embodiments within the scope of the following claims.

We claim:
1. A composition for treating ocular effects of diabetes, comprising:
   a topical carrier having by weight about 0.4% carbomer, 4.0% sorbitol, 0.01% cetrimide, and 0.01% ethylenediaminetetraacetic acid, the balance being water; and
   an aldose reductase inhibitor mixed with the topical carrier to form an ophthalmic gel,
   wherein the topical carrier has a viscosity of about 1,928 cps prior to admixture with the aldose reductase inhibitor, and
   wherein the aldose reductase inhibitor has a standardized particle size of less than 10 microns.

2. The composition for treating ocular effects of diabetes as recited in claim 1, wherein said aldose reductase inhibitor is 2-methyl sorbinil, having the structure:

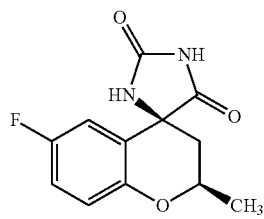 [SMILES: C[C@@H]1C[C@]2(NC(=O)NC2=O)c2cc(F)ccc2O1]

or a pharmaceutically acceptable salt thereof, the aldose reductase inhibitor being between about 0.1% to about 6% by weight of the ophthalmic gel.

3. The composition for treating ocular effects of diabetes as recited in claim 1, wherein the topical carrier further comprises an effective amount of sodium hydroxide for adjusting the pH to about 7.

4. The composition for treating ocular effects of diabetes as recited in claim 1, wherein the topical carrier further comprises an effective amount of sodium chloride for adjusting the viscosity to about 1,300 cps.

5. The composition for treating ocular effects of diabetes as recited in claim 1, wherein the topical carrier has a pH of about 7.

6. The composition for treating ocular effects of diabetes as recited in claim 1, wherein the ophthalmic gel has a viscosity of about 1,300 cps.

7. The composition for treating ocular effects of diabetes as recited in claim 1, wherein said aldose reductase inhibitor is 2-methyl sorbinil, having the structure:

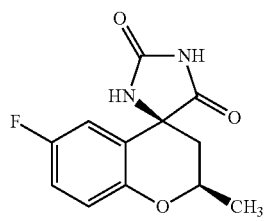 [SMILES: C[C@@H]1C[C@]2(NC(=O)NC2=O)c2cc(F)ccc2O1]

or a pharmaceutically acceptable salt thereof, the aldose reductase inhibitor being between about 0.1% to about 3% by weight of the ophthalmic gel.

8. The composition for treating ocular effects of diabetes as recited in claim 1, wherein said aldose reductase inhibitor is 2-methyl sorbinil, having the structure:

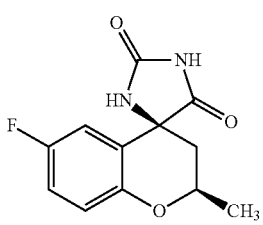

or a pharmaceutically acceptable salt thereof, the aldose reductase inhibitor being between about 3% to about 6% by weight of the ophthalmic gel.

9. A method for treating ocular effects of diabetes, comprising the step of administering an effective amount of a topical composition to a patient's eye, wherein the effect is inhibiting the formation and progression of defects of the cornea and conjunctiva, diabetic cataracts, and diabetic retinopathy, the topical composition comprising:
a topical carrier having by weight about 0.4% carbomer, 4.0% sorbitol, 0.01% cetrimide, and 0.01% ethylenediaminetetraacetic acid, the balance being water; and
an aldose reductase inhibitor mixed with the topical carrier to form an ophthalmic gel
wherein the topical carrier has a viscosity of about 1,928 cps prior to admixture with the aldose reductase inhibitor, and
wherein the aldose reductase inhibitor has a standardized particle size of less than 10 microns.

10. The method for treating ocular effects of diabetes as recited in claim 9, wherein said aldose reductase inhibitor is 2-methyl sorbinil, having the structure:

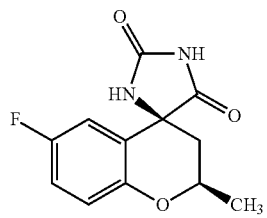

or a pharmaceutically acceptable salt thereof, the aldose reductase inhibitor being between about 0.1% to about 6% by weight of the ophthalmic gel.

11. The method for treating ocular effects of diabetes according to claim 10, wherein:
the patient is a dog; and
the aldose reductase inhibitor comprises between about 3% to about 6% by weight of the ophthalmic gel.

12. The method for treating ocular effects of diabetes according to claim 10, wherein:
the patient is a human; and
the aldose reductase inhibitor comprises between about 0.1% to about 3% by weight of the ophthalmic gel.

13. The method for treating ocular effects of diabetes as recited in claim 9, wherein the step of administering the effective amount of the topical composition comprises topically administering between two and four drops daily to the eye.

14. A method for treating ocular effects of diabetes, comprising the step of administering an effective amount of a topical composition to a patient's eye, wherein the effect is treatment of defects of the cornea and conjunctiva, diabetic cataracts, and diabetic retinopathy, the topical composition comprising:
a topical carrier having by weight about 0.4% carbomer, 4.0% sorbitol, 0.01% cetrimide, and 0.01% ethylenediaminetetraacetic acid, the balance being water; and
an aldose reductase inhibitor mixed with the topical carrier to form an ophthalmic gel,
wherein the topical carrier has a viscosity of about 1,928 cps prior to admixture with the aldose reductase inhibitor, and
wherein the aldose reductase inhibitor has a standardized particle size of less than 10 microns.

15. The method for treating ocular effects of diabetes as recited in claim 14, wherein said aldose reductase inhibitor is 2-methyl sorbinil, having the structure:

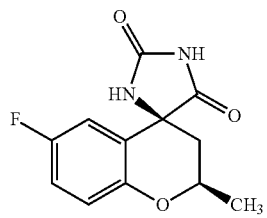

or a pharmaceutically acceptable salt thereof, the aldose reductase inhibitor being between about 0.1% to about 6% by weight of the ophthalmic gel.

16. The method for treating ocular effects of diabetes according to claim 15, wherein:
the patient is a dog; and
the aldose reductase inhibitor comprises between about 3% to about 6% by weight of the ophthalmic gel.

17. The method for treating ocular effects of diabetes according to claim 15, wherein:
the patient is a human; and
the aldose reductase inhibitor comprises between about 0.1% to about 3% by weight of the ophthalmic gel.

18. The method for treating ocular effects of diabetes as recited in claim 15, wherein the step of administering the effective amount of the topical composition comprises topically administering between two and four drops daily to the eye.

* * * * *